United States Patent [19]

Binder

[11] Patent Number: 4,634,418
[45] Date of Patent: Jan. 6, 1987

[54] HYDROGEL SETON

[76] Inventor: Perry S. Binder, P.O. Box 1097, Rancho Santa Fe, Calif. 92067

[21] Appl. No.: 597,530

[22] Filed: Apr. 6, 1984

[51] Int. Cl.⁴ ............................................. A61M 27/00
[52] U.S. Cl. ......................................... 604/8; 604/93; 604/294; 623/4
[58] Field of Search ...................... 604/8, 93, 175, 264, 604/294; 3/1, 13; 623/4

[56] References Cited

U.S. PATENT DOCUMENTS

| | | | |
|---|---|---|---|
| 3,915,172 | 10/1975 | Witcherle et al. | 604/8 |
| 3,948,271 | 4/1976 | Akiyama | 604/49 |
| 4,021,382 | 5/1977 | Stoy et al. | 3/1 |
| 4,428,746 | 1/1984 | Mendez | 604/8 |
| 4,521,210 | 6/1985 | Wong | 604/8 |

OTHER PUBLICATIONS

Surgical Management of Chronic Glaucoma in Aphakia; A. Robert Bellows, MD, Murray A. Johnstone, MD; *Ophthalmology*, vol. 90, No. 7, Jul. 1983.
Long-Term Results of Valve Implants in Filtering Surgery for Eyes with Neovascular Glaucoma; Theodore Krupin, MD, Paul Kaufman, MD, Alan I. Mandell, MD, Stuart A. Terry, MD, Robert Ritch, MD, Steven M. Podos, MD and Bernard Becker, MD; *American Journal of Ophthalmology*, vol. 95, No. 6, Jun. 1983.
The Mai Hydrophilic Implant for Scleral Buckling: A Review, *Ophthalmic Surgery;* Ho, P. C., Chan, I. M., Refojo, M. F. and Tolentino, F. I., vol. 15, pp. 511–515, 1984.
Experimental Seton Procedures in Rabbits; Bloomenthal, M., Harris, L. S., Gaylen, M. A., *Surgical Forum*, vol. 20, 1969. (No. pages listed).
Silicon Catheters used as Setons in Glaucoma Surgery; Egerer, I., *Glaucoma*, vol. 5, No. 1, pp. 32–34, 1983.
Draining Implant for Neovascular Glaucoma; Kuljaca, Z., Ljubojevic, V., Momirov, D., *American Journal of Ophthalmology*, vol. 96, pp. 372–276, 1983.
Anterior Chamber Tube Shunt to an Encircling Band in the Treatment of Neovascular Glaucoma, Schocket, S. S., Lakhantal, V., and Richards, R. D., *Ophthalmology*, vol. 89, pp. 1188–1194, 1982.
Gold Leaf Seton for Lowering Intraocular Pressure; Wolkowicz, M. I., Krishna, N. and Hallett, J. W., *Annals of Opthalmology*, vol. 2, pp. 527–541, 1971.
Valve Implants in Filtering Surgery; Krupin T., Podos, S. M., and Becker, B., and Newkirk, J. B., *American Journal of Ophthalmology*, vol. 81, pp. 232–235, 1976.
Preservation of Ultrastructure of Cells Cultured on Protein-Hydroxyethylmethacrylate Hydrogels; Toselli, P., Farris, B., Oliver, P., Wedel, N., and Franzblau, C., *A Journal of Ultrastructure Research*, vol. 83, pp. 220–231, 1983.
Hydrogel Keratophakia in Non-Human Primates; Binder, P. S., Deg, J. K., and Zavala, E. Y., *Current Eye Res.*, 1:535, 1982.
Hydrogel Implants for the Correction of Myopia; Binder, P. S., *Current Eye Res.*, 2:7, 1981/1983.
Hydrophilic Lenses for Refractive Keratoplasty; The Use of Factory Lathed Materials; Binder, P. S., Baumgartner, S. D., Deg, J. K., Zavala, E. Y., *Clao Journal*, 10:105, 1984.
Hydrogel Refractive Keratoplasty; Lens Removal and Exchanges; Binder, P. S., Zavala, E. Y., Deg, J. K., *Cornea*, 2:119, 1984.
Morphology of Hydrogel Implants used for Refractive Keratoplasty; Samples, J. R., Binder, P. S., Baumgartner, S. D., *Invest Ophthalmol Vis. Sci.*, 25:843, 1984.
Alloplastic Corneal Implants for the Correction of Refractive Errors; Binder, P. S., Zavala, E. Y., Baumgartner, S. D., Deg, J. K., *Ophthalmology*, 91:806, 1984.

*Primary Examiner*—P. E. Konopka
*Attorney, Agent, or Firm*—Lyon & Lyon

[57] ABSTRACT

A seton constructed of a hydrogel material is surgically implanted in the anterior chamber of the eye in order to alleviate intraocular pressure. Once implanted, the seton acts as a wick due to its porosity to reduce the intraocular pressure. The material from which the seton is constructed is a material which is biocompatible with the tissue of the eye and allows fluid within the eye to migrate about the seton without bacterial ingress to the eye, such as for example, a hydrogel material having a water content ranging from 30% to 79%.

15 Claims, 5 Drawing Figures

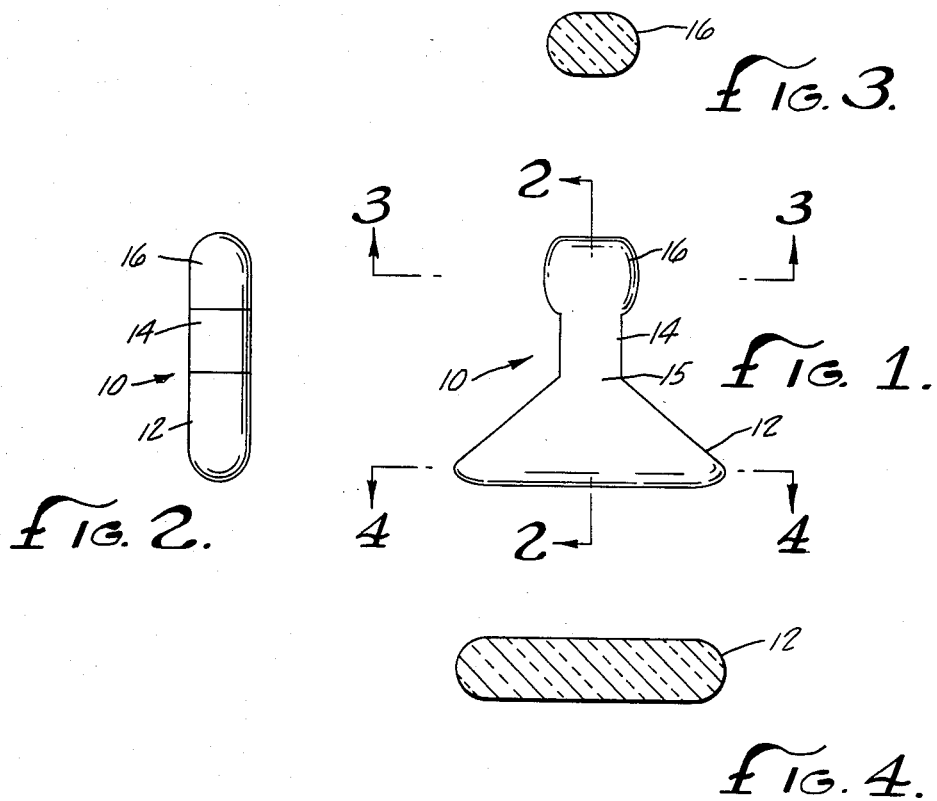
Fig. 3.
Fig. 2.
Fig. 1.
Fig. 4.
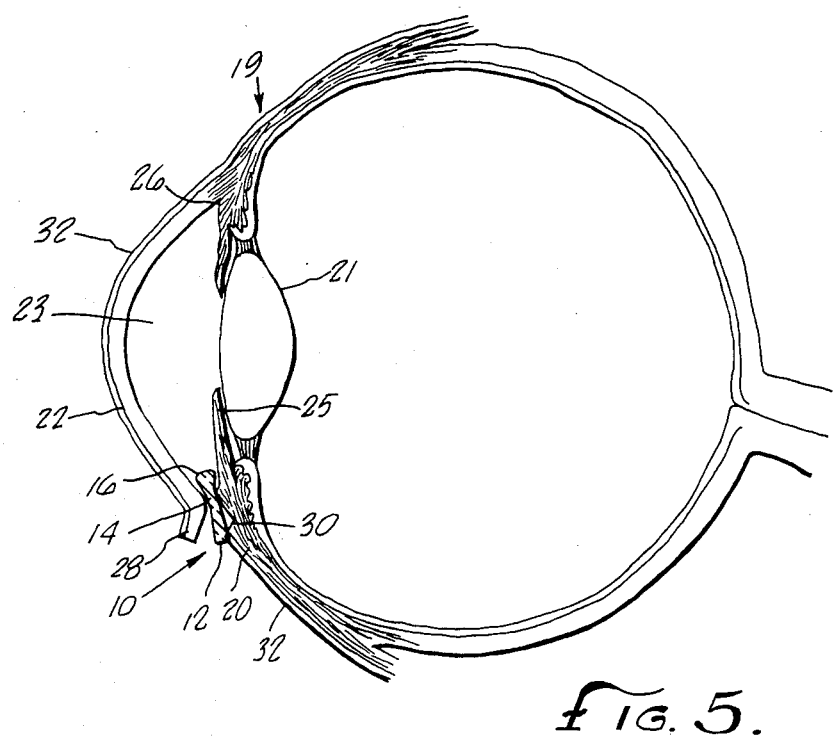
Fig. 5.

HYDROGEL SETON

BACKGROUND OF THE INVENTION

The field of the invention is treatment of eye disorders, and more particularly setons used to treat uncontrolled intraocular pressure.

Glaucoma is a disease of the eye which affects a substantial number of people. It involves uncontrolled intraocular pressure within the eye caused by obstruction of the trabecular meshwork and causes permanent damage to the optic nerve. Surgical treatment of glaucoma has been limited due to failure to control intraocular pressure as well as post-operative complications which tend to exacerbate the pre-operative increased intraocular pressure.

The eye is a complex organ. The front of the eye is covered by the cornea. The cornea refracts light through the anterior chamber to the lens. Muscles control the size of the entrance aperture of the eye, also known as the pupil. The lens is suspended by the iris and focuses the refracted light through the vitreous chamber and onto the retina in the back of the eye. The shape of the lens can be varied by muscles within the eye to focus on objects that are close or far away.

Normally, the fluid within the eye, known as aqueous humor is produced by the ciliary body and migrates through the pupil, into the anterior chamber, through the trabecular meshwork and into the aqueous veins which form fluid collection channels beneath the conjunctiva. Glaucoma results when the intraocular pressure is not relieved by aqueous migration. This is typically due to obstruction of the trabecular meshwork. The uncontrolled high pressure of glaucoma leads to permanent damage of the optic nerve.

Medical treatment of the uncontrolled high pressure of glaucoma has had varying success. Medicines in the form of eye drops or pills to reduce the production of aqueous in the ciliary body and/or increase the outflow of aqueous through the trabecular meshwork are often used. In some cases, surgical filtration procedures are attempted. One such technique creates a hole through the limbus and excises a piece of the trabecular meshwork. After filtration surgery, the aqueous will flow from the anterior chamber through the excised surgical area and into the space beneath the conjunctiva where it is finally absorbed by the body.

Another attempt to improve the filtration through the trabecular meshwork involves placing several Argon laser burns throughout the enter circumference of the trabecular meshwork in hopes of opening up the trabecular meshwork spaces. This procedure is called Argon laser trabeculoplasty.

In certain high risk cases, these surgical techniques are typically unsuccessful due to the post-operative scarring of the wound or the scleral tissue. This scarring prevents migration of the aqueous out of the eye and results in a recurrence of the uncontrolled intraocular pressure of glaucoma.

Another method to attempt to relieve the uncontrolled high pressure of glaucoma is to perform an iridencleisis. The procedure involves pulling a piece of the iris through a wound cut into the anterior chamber. Serious infection and inflammation of the wound often results from this procedure. In addition, a piece of cartilage has been implanted into the eye in an attempt to control glaucoma. This procedure failed due to scar tissue forming about the wound and the closure preventing migration of aqueous. Finally, seton implants in the form of polypropylene tubing and a Krupin Valve implant have failed due to post-operative extrusion of the implants through the wound as well as the formation of clots which act to inhibit the flow of aqueous.

In cases where medicines, laser trabeculoplasty and surgical filtration procedures, such as a trabeculectomy, have failed, the only medically proven method for controlling pressure within the eye is to permanently damage the ciliary body. This procedure, known as Cyclocrytherapy, involves externally freezing the sclera above the ciliary body. This process damages any potentially functioning trabecular meshwork and is frought with complications, such as bleeding within the eye and other significant damage to the eye, thereby causing loss of use of the eye.

SUMMARY OF THE INVENTION

In order to reduce excessive intraocular pressure it is necessary to allow aqueous to migrate out of the eye. The invention disclosed herein is a device which is biocompatible with the tissue in the eye and allows fluid to migrate through the device to the space under the conjunctiva without allowing bacteria to ingress into the eye. The seton is made of a porous material, such as a hydrogel material having a water content ranging from 30% to 79% (hereinafter hydrogel), and is surgically implanted in the eye. The seton is shaped so as to retain its position once implanted and provides adequate surface area to accommodate the passage of the aqueous. The seton acts as a conduit for fluid to migrate from the inner portion of the eye outwards. Intraocular pressure is thereby reduced in a controlled fashion while preventing bacteria from entering the eye.

An object of the invention is to provide a means for treating the excessive intraocular pressure symptomatic of glaucoma which is biocompatible with the tissue of the eye.

An additional object of the invention is to provide a means to relieve intraocular pressure in a controlled fashion which prevents bacteria from entering the eye.

A further object of the invention is to provide an intraocular pressure relief device which will retain its position once surgically implanted within the eye.

A further object of the invention is to provide a means for relieving intraocular pressure which will not permanently damage the eye or its ability to function normally.

A further object of the invention is to provide a means for relieving the excessive intraocular pressure of glaucoma which will not be defeated by subsequent scarring of the tissue of the eye. Other and more detailed objects and advantages of the invention will become apparent from examination of the description and drawings herein.

DETAILED DESCRIPTION OF THE DRAWINGS

FIG. 1 is a front view of an embodiment of the seton;

FIG. 2 is a side view of an embodiment of the seton;

FIG. 3 is a cross-sectional view of an embodiment of the seton taken substantially along line 3—3 of FIG. 1;

FIG. 4 is a cross-sectional view of an embodiment of the seton taken substantially along line 4—4 of FIG. 1; and, FIG. 5 is a cross-sectional view showing an embodiment of the seton implanted in an eye.

DETAILED DESCRIPTION OF THE INVENTION

As shown in FIGS. 1-4, the seton 10 has a base portion 12 which is essentially triangular in shape. A neck portion 14 extends from the upper corner 15 of the triangular base portion 12. A lip portion 16 is formed about the upper end of the neck portion 14 furthest from the triangular base portion 12. As can be seen clearly in FIGS. 2-4, the seton has a cross-section which varies from an ellipse at the lip end 16 to an oval at the lower end of triangular base 12.

The seton 10 is implanted into the eye 19, as illustrated in FIG. 5. A trabeculectomy procedure is performed under a limbus-based conjunctival flap by dissecting a rectangular piece of sclera 20 5 mm×5 mm in partial thickness into the clear cornea. An incision is made into the anterior chamber 23 using razor blade fragments on both sides of the subscleral wound to permit a rectangular-sized piece of cornea 22, Schalbe's line and a portion of the filtration meshwork 26 measuring 2 mm in vertical height and 3 to 4 mm in length to be removed from the eye. The bed of the wound is appropriately cauterized to prevent bleeding. An iridectomy is performed only if the iris 25 prolapses into the wound.

A seton 10 as described hereinabove, with previously factory lathed edges is inserted into the wound. The seton 10 is made from a hydrogel material having a water content which ranges from 30% to 79% (hereinafter hydrogel). The lip portion 16 of the seton 10 which fits into the anterior chamber 23 is slightly larger than the incision in the anterior chamber 23. By compressing the lip portion 16 of the seton 10 prior to insertion into the anterior chamber 23, the subsequent expansion of the lip portion 16 will act to maintain the position of the seton 10. The lip portion 16 thereby acts to prevent extrusion of the seton 10 into the subscleral space 30. The scleral flap 28 is then closed over the seton 10 with 2 interrupted 10-0 monofilament nylon sutures at the apices of the wound. So implanted, only the corners of the lower end of the triangular base 12 of the seton 12 will protrude from beneath the sutured scleral flap 28. The conjunctiva 32 is then closed over the entire surgical area with a continuous 10-0 monofilament nylon suture.

For purposes of example, the preferred embodiment of the seton 10, as shown in FIG. 1, is approximately 6 to 8 mm in length and approximately 7 to 9 mm in width at the base of the triangular portion 12. The neck portion 14 is approximately 2 mm in diameter while the lip portion is approximately 3 to 4 mm in diameter. Similarly, as shown in FIGS. 2-4, the preferred embodiment of the invention is approximately ½ mm thick.

It is possible to attach a polypropylene suture (not shown) to the seton 10 so that it may be postoperatively retracted from its subscleral position should the eye become excessively soft, a condition known as hypotonous. In addition, the seton 10 may be colored to enable easy visualization of the seton in the eye.

When properly inserted, seton 10 acts to allow aqueous within the eye to migrate from the anterior chamber 23 to the space beneath the scleral flap 28. Serious infection of the eye is prevented since the hydrogel material from which the seton 10 is constructed will not allow bacterial ingress to the anterior chamber 23 through the seton 10.

While described hereinabove in detail, the description contained herein is for purposes of example only and should not be construed to limit the scope of the appended claims.

We claim:

1. A seton for reducing intraocular pressure comprising a body portion, said body portion being substantially triangular in shape and having a cross-section which varies from substantially elliptical to substantially oval, a neck portion extending from said body portion, a lip portion formed about said neck portion, said seton being constructed from a biocompatible porous hydrogel material and said seton further including a peripheral edge.

2. A seton as set forth in claim 1 wherein said lip portion is at the end of said neck portion farthest from said body portion.

3. A seton as set forth in claim 1 wherein said seton material is a hydrogel material having a water content ranging from 30% to 79%.

4. A seton as set forth in claim 3 wherein said seton peripheral edge is substantially rounded.

5. A seton for reducing intraocular pressure comprising a body portion, said body portion being substantially triangular in shape and having a cross section which varies from substantially elliptical to substantially oval, a neck portion extending from said body portion, a lip portion formed about said neck portion at the end of said neck portion farthest from said body portion, said seton being constructed from a biocompatible porous hydrogel material having a water content ranging from 30% to 79% and, said seton further including a peripheral edge which is substantially rounded.

6. A seton for relieving intraocular pressure comprising,
a body portion which is substantially triangular in shape and whose cross-section varies from substantially elliptical to substantially oval;
a neck portion extending from one corner of said body portion; and,
a lip portion formed about said neck portion, said seton being constructed from a biocompatible porous hydrogel material.

7. A seton as set forth in claim 6 wherein said lip portion is at the end of said neck portion farthest from said body portion.

8. A seton as set forth in claim 6 wherein said biocompatible material is a hydrogel material having a water content ranging from 30% to 79%.

9. A seton for relieving intraocular pressure comprising,
a body portion and a lip portion, said body portion having a first end, said first end having a narrowed portion which is arranged for insertion into the anterior chamber of a human eye, said lip portion being formed on said narrowed portion of said first end of said body portion to inhibit the extrusion of said first end of said seton from the eye when said seton is implanted in the eye and said body portion being of a similar size or larger than said lip portion to prevent said seton from being drawn into the eye after said seton is implanted into the eye, said body portion and said lip portion being formed from a biocompatible porous hydrogel material.

10. A seton as set forth in claim 9 wherein said body portion is substantially triangular in shape.

11. A seton for reducing excessive intraocular pressure caused by glaucoma, comprising, a body portion, said body portion being substantially triangular in shape and having a cross section which varies from substantially elliptical to substantially oval, a neck portion extending from said body portion and a lip portion formed about said neck portion at the end of said neck portion farthest from said body portion, said seton being constructed from a biocompatible porous hydrogel material having a water content ranging from 30% to 79%.

12. A method for reducing intraocular pressure, the steps comprising,
creating a limbus-based conjunctiva and scleral flap by making an incision near the junction of the cornea and the sclera,
excising a portion of the cornea, Schalbe's line and the trabecular meshwork by making incisions into the anterior chamber beneath said flap,
inserting a first end of a seton beneath said flap, said seton being constructed from a biocompatible porous hydrogel material and including a body portion and a lip portion, said lip portion being formed on said first end of said seton, said body portion having a peripheral edge,
suturing said flap about said seton such that said seton extends radially from the anterior chamber to the space beneath said flap and such that at least a portion of said seton extends from beneath said sutured flap, and
closing the conjunctiva about said flap and said seton.

13. The method as set forth by claim 12 wherein said seton is made from a hydrogel material having a water content ranging from 30% to 79%.

14. The method as set forth by claim 13 wherein said seton first end which is inserted in said incision through the sclera is larger than said incision so as to maintain the position of said seton when implanted and said body portion of said seton is substantially triangular in shape and has a cross-section which varies from substantially elliptical to substantially oval.

15. A method for reducing excessive intraocular pressure caused by glaucoma, the steps comprising, creating a limbus-based conjuctival and scleral flap by making an incision near the junction of the cornea and the sclera, excising a portion of the cornea, Schalbe's Line and the trabecular meshwork by making an incision into the anterior chamber beneath said flap, inserting a first end of a seton beneath said flap, said seton being constructed from a biocompatible porous hydrogel material and including a body portion, a neck portion and a lip portion, said neck portion extending from said body portion, said lip portion being formed about said neck portion at the end of said neck portion farthest from said body portion, suturing said flap about said seton such that said seton extends radially from the anterior chamber of the eye into the space beneath said flap and such that at least a portion of said seton body is exposed beneath said sutured flap, and closing the conjunctiva about said flap and said seton.

* * * * *